(12) United States Patent
Prokop (10) Patent No.: US 11,129,672 B2
(45) Date of Patent: Sep. 28, 2021

(54) TISSUE RESECTING DEVICE INCLUDING AN ARTICULATABLE CUTTING MEMBER

(71) Applicant: COVIDIEN LP, Mansfield, MA (US)

(72) Inventor: Paul F. Prokop, Woburn, MA (US)

(73) Assignee: Covidien LP, Mansfield, MA (US)

( * ) Notice: Subject to any disclaimer, the term of this patent is extended or adjusted under 35 U.S.C. 154(b) by 270 days.

(21) Appl. No.: 16/375,601

(22) Filed: Apr. 4, 2019

(65) Prior Publication Data

US 2020/0315693 A1 Oct. 8, 2020

(51) Int. Cl.
*A61B 18/14* (2006.01)
*A61B 17/42* (2006.01)
*A61B 18/00* (2006.01)

(52) U.S. Cl.
CPC .......... *A61B 18/1445* (2013.01); *A61B 17/42* (2013.01); *A61B 18/1485* (2013.01); *A61B 2017/4216* (2013.01); *A61B 2018/00601* (2013.01); *A61B 2018/1412* (2013.01)

(58) Field of Classification Search
CPC ............ A61B 18/1445; A61B 18/1485; A61B 2018/00601; A61B 17/32002; A61B 17/320758; A61B 17/320725; A61B 2017/320791; A61B 2017/320775; A61B 2017/320766; A61B 17/32075; A61B 2017/4216; A61B 2018/1412; A61B 17/42; A61B 2017/00309; A61B 17/320783
See application file for complete search history.

(56) References Cited

U.S. PATENT DOCUMENTS

| | | | |
|---|---|---|---|
| 5,085,658 A | 2/1992 | Meyer | |
| 5,226,909 A * | 7/1993 | Evans | A61B 17/320783 604/22 |
| 5,437,630 A * | 8/1995 | Daniel | A61B 17/32002 604/22 |
| 5,529,580 A | 6/1996 | Kusunoki et al. | |
| 5,620,447 A * | 4/1997 | Smith | A61B 17/32002 604/22 |
| 5,669,926 A * | 9/1997 | Aust | A61B 17/32002 606/170 |
| 5,690,660 A | 11/1997 | Kauker et al. | |
| 5,766,199 A | 6/1998 | Heisler et al. | |
| 5,947,983 A * | 9/1999 | Solar | A61B 17/0469 606/144 |

(Continued)

*Primary Examiner* — Katrina M Stransky
(74) *Attorney, Agent, or Firm* — Carter DeLuca & Farrell LLP (57) ABSTRACT

An end effector assembly of a tissue resecting device includes a cutting member and an elongated outer shaft. The cutting member includes a core defining a passage and a plurality of blades extending radially outward from the core. Adjacent blades define a gap therebetween. The plurality of blades defines at least one window in communication with the passage of the core. The elongated outer shaft includes a tool portion rotatably receiving the plurality of blades of the cutting member therein. The tool portion defines a lateral opening such that the plurality of blades of the cutting member rotatably received in the tool portion is in registration with the lateral opening. The cutting member is transitionable between a neutral position, in which, the cutting member defines a longitudinal axis, and an articulated position, in which, at least a portion of the cutting member is offset from the longitudinal axis.

15 Claims, 4 Drawing Sheets

(56) References Cited

U.S. PATENT DOCUMENTS

| | | | |
|---|---|---|---|
| RE38,018 E | 3/2003 | Anctil et al. | |
| 7,699,846 B2* | 4/2010 | Ryan | A61B 17/32002 606/50 |
| 8,528,563 B2 | 9/2013 | Gruber | |
| 2003/0114875 A1* | 6/2003 | Sjostrom | A61B 17/32002 606/170 |
| 2008/0097470 A1 | 4/2008 | Gruber et al. | |
| 2013/0023882 A1* | 1/2013 | Fabro | A61B 17/295 606/80 |
| 2014/0012255 A1 | 1/2014 | Smith et al. | |
| 2015/0066033 A1* | 3/2015 | Jorgensen | A61B 1/00087 606/79 |
| 2015/0282833 A1* | 10/2015 | Yoon | A61B 17/320758 606/114 |
| 2019/0038305 A1* | 2/2019 | Smith | A61B 17/1659 |

* cited by examiner

TISSUE RESECTING DEVICE INCLUDING AN ARTICULATABLE CUTTING MEMBER

BACKGROUND

1. Technical Field

The present disclosure relates generally to the field of tissue resection. In particular, the present disclosure relates to a tissue resecting device including an articulatable cutting member.

2. Background of Related Art

Tissue resection may be performed endoscopically within an organ, such as a uterus, by inserting an endoscope (or hysteroscope) into the uterus and passing a tissue resection device through the endoscope (or hysteroscope) and into the uterus. With respect to such endoscopic tissue resection procedures, it is often desirable to distend the uterus with a fluid, for example, saline, sorbitol, or glycine. The inflow and outflow of the fluid during the procedure maintains the uterus in a distended state and flushes tissue and other debris from within the uterus to maintain a visible working space.

SUMMARY

As used herein, the term "distal" refers to the portion that is described which is farther from a user, while the term "proximal" refers to the portion that is described which is closer to a user. Further, to the extent consistent, any or all of the aspects described herein may be used in conjunction with any or all of the other aspects described herein.

In accordance with an aspect of the present disclosure, an end effector assembly of a tissue resecting device includes a cutting member and an elongated outer shaft. The cutting member includes a core defining a passage and a plurality of blades extending radially outward from the core. Adjacent blades define a gap therebetween. The plurality of blades defines at least one window in communication with the passage of the core. The elongated outer shaft includes a tool portion rotatably receiving the plurality of blades of the cutting member therein. The tool portion defines a lateral opening such that the plurality of blades of the cutting member rotatably received in the tool portion is in registration with the lateral opening. The cutting member is transitionable between a neutral position, in which, the cutting member defines a longitudinal axis, and an articulated position, in which, at least a portion of the cutting member is offset from the longitudinal axis.

In an aspect, the plurality of blades of the cutting member may be arranged along a length of the core.

In another aspect, the cutting member may be rotatable between an open position, in which, the at least one window of the cutting member is in registration with the lateral opening of the elongated outer shaft, and a closed position, in which, the at least one window is offset relative to the lateral opening of the elongated outer shaft.

In yet another aspect, the cutting member may be rotatable in the articulated position.

In still yet another aspect, the cutting member may be articulatable in a range of about 0 degree and about 90 degrees.

In an aspect, each blade of the plurality of blades defines the at least one window may include a cutting edge configured to cut tissue.

In another aspect, first and second windows of the at least one window of the plurality of blades may diametrically oppose each other.

In yet another aspect, first and second windows of the at least one window of the plurality of blades may be arranged along at least a portion of a length of the cutting member.

In still yet another aspect, the cutting member may include a blunt tip distal of the plurality of blades.

In still yet another aspect, the tool portion of the elongated outer shaft may include a plurality of articulation members. Adjacent articulation members may define a slit therebetween.

In yet another aspect, each slit may extend away from the lateral opening.

In an aspect, the slits defined in the tool portion may be in registration with the respective gaps defined in the cutting member.

In another aspect, the elongated outer shaft may further include an articulation cable coupled to a distal portion of the elongated outer shaft, such that axial displacement of the cable causes articulation of the cutting member between the neutral position and the articulated position.

In yet another aspect, the elongated outer shaft may further include a guide member configured to receive the articulation cable therethrough.

In still yet another aspect, the guide member may be disposed on one articulation member of the plurality of articulation members.

In accordance with another aspect of the present disclosure, a tissue resecting device includes a handpiece assembly including a drive rotor, and an end effector assembly including a cutting member coupled with the drive rotor for concomitant rotation therewith, and an elongated outer shaft. The cutting member includes a core defining a passage and a plurality of blades arranged along a length of the core. Adjacent blades define a gap therebetween. The plurality of blades defines at least one window in communication with the passage of the core. The cutting member is transitionable between a neutral position, in which, the cutting member defines a longitudinal axis, and an articulated position, in which, at least a portion of the cutting member extends laterally outward from the longitudinal axis. The elongated outer shaft is operatively coupled with the handpiece assembly. The elongated outer shaft includes a tool portion configured to rotatably receive the cutting member therein. The tool portion defines a lateral opening such that when the cutting member is rotatably received in the tool portion, the plurality of blades is in registration with the lateral opening of the tool portion.

In an aspect, the elongated outer shaft may further includes a cable including a distal portion coupled to a distal portion of the elongated outer shaft such that axial displacement of the cable transitions the cutting member between the neutral and articulated positions.

In another aspect, the at least one window of the plurality of blades may be in registration with the lateral opening of the elongated outer shaft when the cutting member is in the articulated position.

BRIEF DESCRIPTION OF THE DRAWINGS

Various aspects and features of the present disclosure are described hereinbelow with reference to the drawings wherein like numerals designate identical or corresponding elements in each of the several views and.

DETAILED DESCRIPTION

Figure 1:
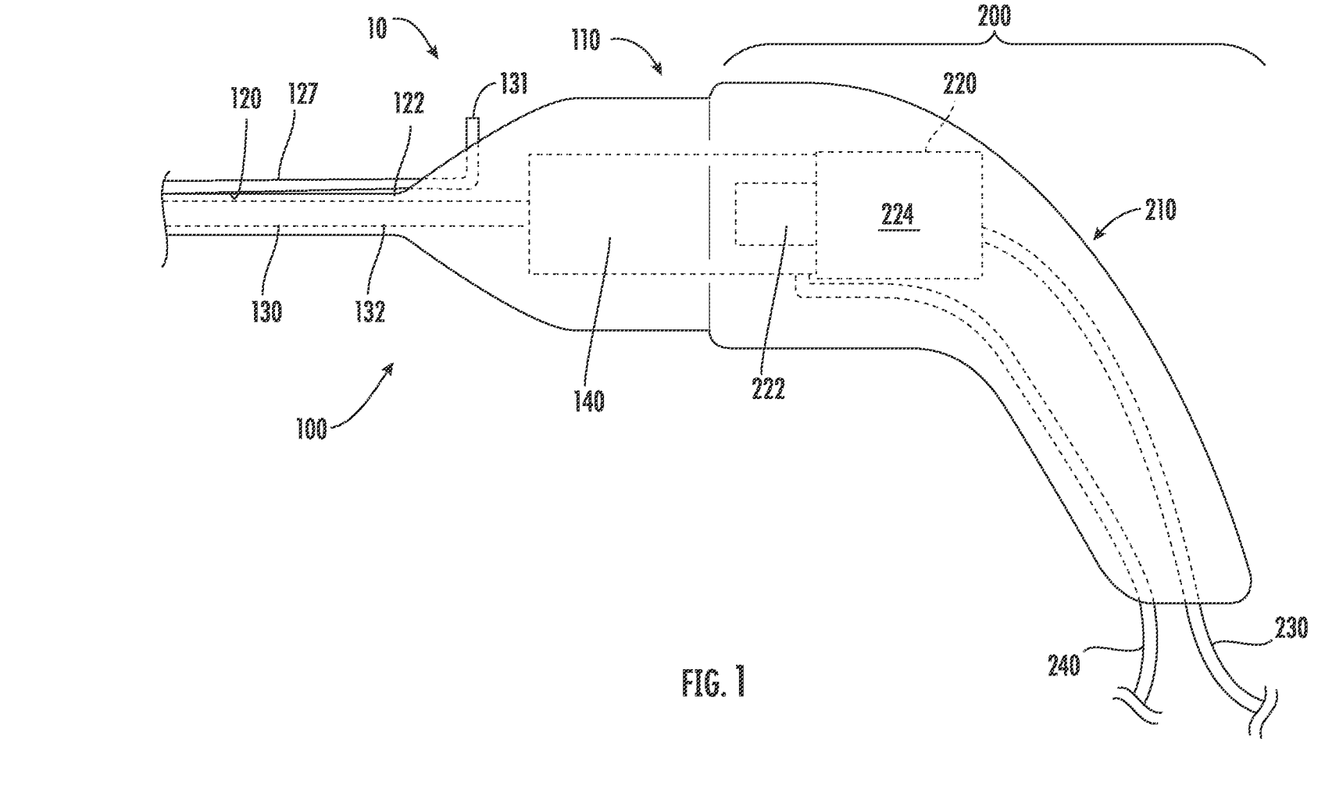
FIG. 1 is a partial side view of a proximal portion of a tissue resecting device in accordance with an aspect of the present disclosure.

Referring generally to FIG. 1, a tissue resecting device 10 provided in accordance with the present disclosure and configured to resect tissue includes an end effector assembly 100 and a handpiece assembly 200. Tissue resecting device 10 is adapted to connect to a control unit (not shown), e.g., via cable 230, to provide power and control functionality to tissue resecting device 10, although tissue resecting device 10 may alternatively or additionally include controls associated with handpiece assembly 200 and/or a power source, e.g., battery, disposed within handpiece assembly 200. In other embodiments, tissue resecting device 10 is manually powered and/or controlled. Tissue resecting device 10 is further adapted to connect to a fluid management system (not shown), e.g., via outflow tubing 240, for removing fluid, tissue, and debris from a surgical site via tissue resecting device 10. The control unit and fluid management system may be integral with one another, coupled to one another, or separate from one another.

With continued reference to FIG. 1, tissue resecting device 10 may be configured as a single-use device that is discarded after use or sent to a manufacturer for reprocessing, a reusable device capable of being cleaned and/or sterilized for repeated use by the end-user, or a partially-single-use, partially-reusable device. With respect to partially-single-use, partially-reusable configurations, handpiece assembly 200 may be configured as a cleanable/sterilizable, reusable component, while end effector assembly 100 is configured as a single-use, disposable/reprocessable component. In either of the above configurations, end effector assembly 100 is configured to releasably engage handpiece assembly 200 to facilitate disposal/reprocessing of any single-use components and cleaning and/or sterilization of any reusable components. Further, enabling releasable engagement of end effector assembly 100 with handpiece assembly 200 allows for use of different end effector assemblies with handpiece assembly 200.

Figure 4:
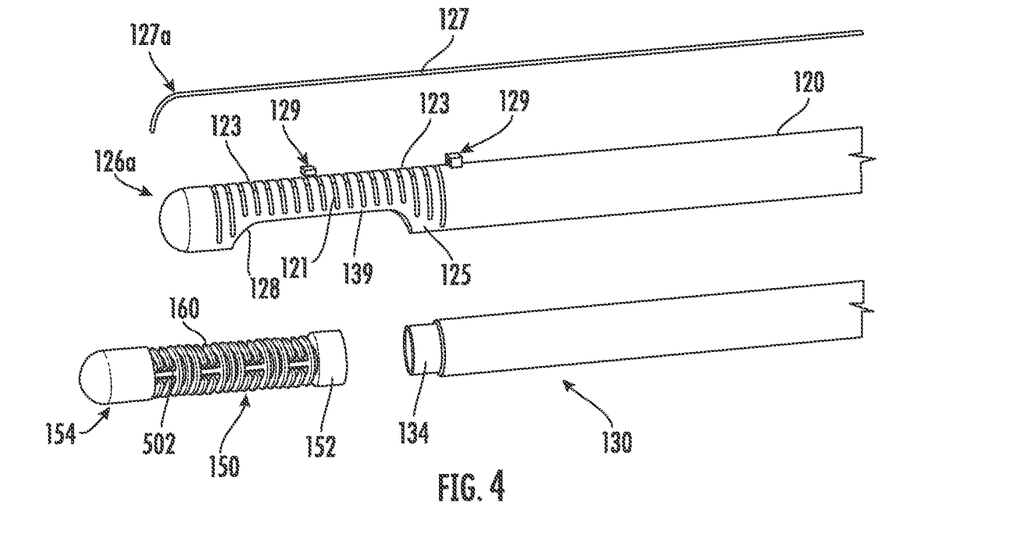
FIG. 4 is an exploded perspective view of the distal portion of the end effector assembly of FIG. 2, with parts separated.

End effector assembly 100 includes a proximal hub housing 110, an elongated outer shaft 120 fixedly engaged with and extending distally from proximal hub housing 110, an inner cutting shaft 130 movably disposed within elongated outer shaft 120, an inner drive core 140, and a cutting member 150 (FIG. 4). Inner drive core 140 is operably disposed within proximal hub housing 110 and coupled to inner cutting shaft 130 such that rotational input imparted to inner drive core 140, e.g., via handpiece assembly 200, drives rotation of inner cutting shaft 130 within and relative to elongated outer shaft 120. In embodiments, inner cutting shaft 130 may be configured to additionally or alternatively reciprocate relative to elongated outer shaft 120.

Proximal hub housing 110 of end effector assembly 100 is configured to releasably engage handle housing 210 of handpiece assembly 200, e.g., via snap-fit, threaded, luer-lock, lock-button, or other suitable engagement, and may be configured for fixed engagement with handle housing 210 or rotational engagement therewith.

Figure 2:
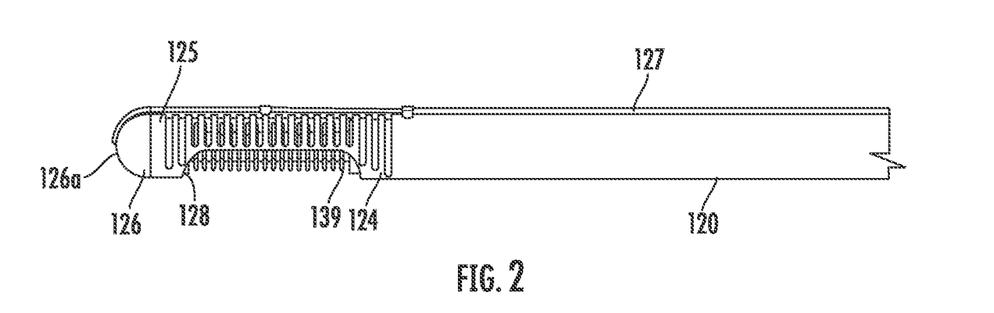
FIG. 2 is a partial side view of a distal portion of an end effector assembly of the tissue resecting device of FIG. 1.

With reference now to FIGS. 1 and 2, elongated outer shaft 120 of end effector assembly 100 includes a proximal end portion 122 extending into and fixedly engaged within proximal hub housing 110, and a distal end portion 124 including a tool portion 125. Elongated outer shaft 120 may be formed as a single construct. For example, elongated outer shaft 120 may be monolithically formed. Tool portion 125 includes a closed distal end 126 having a blunt tip 126a and defines a window 128 proximally-spaced from closed distal end 126. Window 128 provides access to the interior of elongated outer shaft 120 and may be surrounded by a cutting edge 139 about the outer perimeter of window 128 so as to facilitate cutting of tissue passing through window 128 and into elongated outer shaft 120. Alternatively, window 128 may define a blunt edge.

Figure 3:
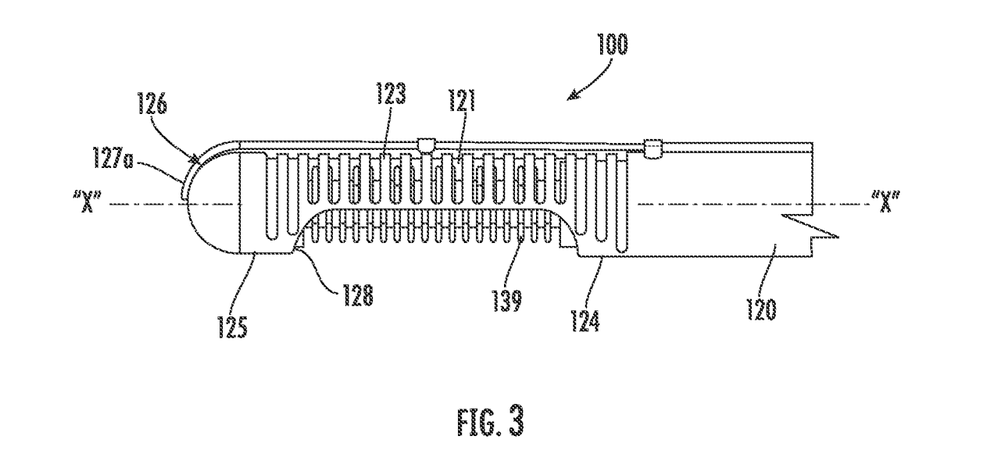
FIG. 3 is a partially enlarged side view of a distal end portion of the end effector assembly of FIG. 2, disposed in a neutral position.
Figure 6:
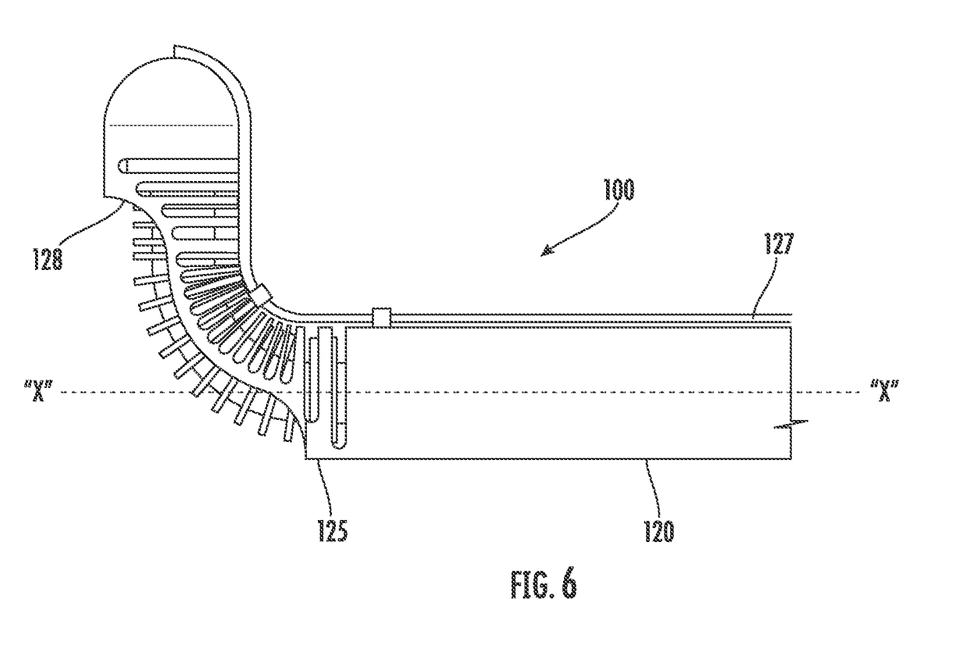
FIG. 6 is a partially enlarged side view of the distal end portion of the end effector assembly of FIG. 2, disposed in an articulated position.

With reference to FIGS. 3 and 4, tool portion 125 of elongated outer shaft 120 includes a plurality of articulation members 123 arranged along a length of tool portion 125. Adjacent articulation members 123 define a slit 121 to enable flexing or articulation of tool portion 125. In particular, each slit 121 extends from a position adjacent a peripheral portion of window 128 to a position adjacent an opposing side of window 128. In order to facilitate articulation of tool portion 125, the lengths of slits 121 may vary. In order to effect articulation of tool portion 125, tool portion 125 further includes an articulation cable 127. In particular, a distal end 127a of articulation cable 127 is fixedly coupled to blunt tip 126a (FIG. 1) of elongated outer shaft 120. Tool portion 125 further includes guide members 129 configured to receive articulation cable 127 therethrough to facilitate axial displacement of articulation cable 127. Under such a configuration, axial displacement of articulation cable 127 effects articulation of tool portion 125 between a neutral position (FIG. 3) and an articulated position (FIG. 6). It is contemplated that a lever or a knob 131 (FIG. 1) may be provided on proximal hub housing 110 of end effector assembly 100 (as shown) or on handpiece assembly 200 (FIG. 1) to effect axial displacement of articulation cable 127.

With reference to FIG. 4, inner cutting shaft 130 includes a proximal end portion 132 (FIG. 1) and a distal end portion 134 coupled to cutting member 150 for concomitant rotation therewith. Cutting member 150 may be detachably coupled to distal end portion 134, e.g., via snap-fit, threaded, luer-lock, lock-button, or other suitable engagement, and may be configured for fixed engagement with inner cutting shaft 130. However, it is also contemplated that cutting member 150 may be monolithically formed with or otherwise permanently connected to inner cutting shaft 130.

Figure 5:
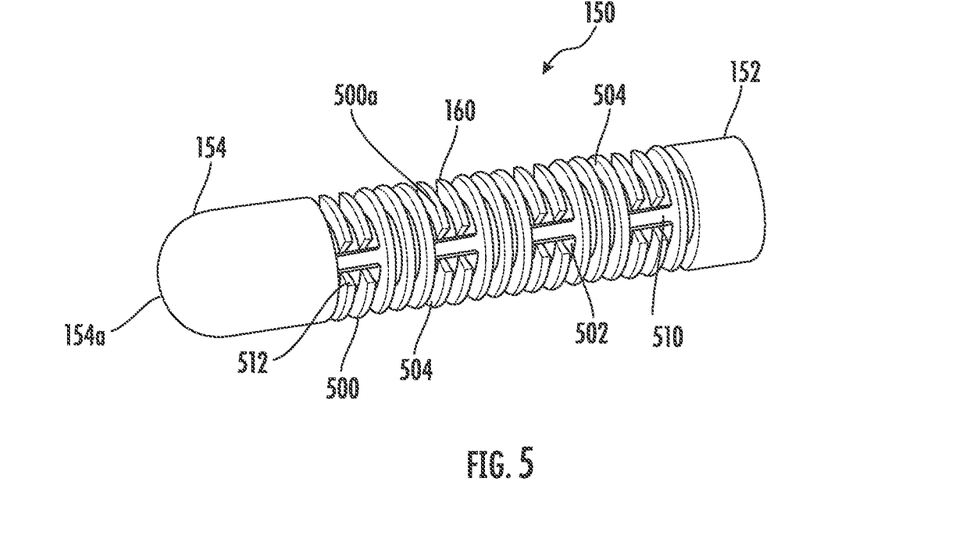
FIG. 5 is a perspective view of a cutting member of the end effector assembly of FIG. 2.

With reference now to FIGS. 4 and 5, cutting member 150 includes an adapter portion 152 configured to be coupled to distal end portion 134 of inner cutting shaft 130, a blade portion 160 extending distally from adapter portion 152, and a closed distal end 154 having a blunt tip 154a configured to be rotatably associated with blunt tip 126a (FIG. 2) of elongated outer shaft 120. Cutting member 150 is rotatably received in tool portion 125 of elongated outer shaft 120. Blade portion 160 may include a bellows configuration. Blade portion 160 includes a flexible core 502 interconnecting adapter portion 152 and closed end portion 154, and a plurality of blades 500 extending radially outward from flexible core 502 and arranged along a length of flexible core 502. Flexible core 502 defines a passage 510 in communication with the interior of inner cutting shaft 130 such that tissue or fluid may be received therethrough.

When cutting member 150 is rotatably received in tool portion 125 (FIG. 3), the plurality of blades 500 is exposed through window 128 of tool portion 125. Adjacent blades 500 define a gap 504 therebetween to enable articulation of cutting member 150. For example, cutting member 150 may be articulatable in a range of about 0 degree and about 90 degrees. In an embodiment, slits 121 (FIG. 3) of tool portion 125 may be in registration with respective gaps 504 of cutting member 150 to further facilitate articulation of cutting member 150 in conjunction with articulation of tool portion 125 of elongated outer shaft 120.

With particular reference to FIGS. 4 and 5, the plurality of blades 500 define windows 512 dimensioned to receive tissue therein. Each window 512 is in communication with passage 510 of flexible core 502. In particular, each blade 500 defining the window 512 includes a cutting edge 500a configured to cut tissue passing through window 128 (FIG. 3) of tool portion 125 (FIG. 3) and into window 512. Blade portion 160 may include a plurality of windows 512. In some embodiments, pairs of windows 512 may diametrically oppose each other to further facilitate cutting of tissue. Windows 512 may additional or alternatively be longitudinally-spaced along at least a portion of the length of blade potion 160.

With continued reference to FIGS. 4 and 5, inner cutting shaft 130 is rotatable relative to elongated outer shaft 120. Inner cutting shaft 130 may be continuously rotated in a single direction or may be configured to reverse and move in opposite directions. In either configuration, rotation of inner cutting shaft 130 relative to elongated outer shaft 120 defines at least one open position of end effector assembly 100, wherein inner cutting shaft 130 is oriented relative to elongated outer shaft 120 such that at least some of windows 512 of cutting member 150 at least partially overlap window 128 of tool portion 125 of elongated outer shaft 120, thus enabling fluid communication therebetween. In the at least one open position, cutting edge 139 is exposed to cut tissue extending through window 128 and into window 512. During rotation of inner cutting shaft 130, at least one window 512 or, in embodiments, all windows 512, is in a closed position, in which, inner cutting shaft 130 is oriented relative to elongated outer shaft 120 such that window(s) 512 does not radially overlap window 128, e.g., the at least one window 512 (or all windows) are displaced relative to window 128, thus inhibiting fluid communication therebetween. The rotation of window(s) 512 between open and closed positions enables cutting of tissue by cutting edge 139 and cutting edge 500a.

Referring back to FIG. 1, handpiece assembly 200 generally includes a handle housing 210, a drive assembly 220 disposed within handle housing 210, a cable 230, and an outflow tubing 240. Handle housing 210 is configured to releasably engage proximal hub housing 110 of end effector assembly 100, and defines a pistol-grip configuration, although other configurations are also contemplated, e.g., a pencil-grip configuration. Handpiece assembly 200 may further include one or more controls (not shown) disposed on or operably associated with handle housing 210 to facilitate activation of drive assembly 220 or displacement of articulation cable 127 in a desired manner. For example, handpiece assembly 200, rather than proximal hub housing 110 of end effector assembly 100 (as shown), may include the dial or lever 131 that is operatively coupled to articulation cable 127 to axially displace articulation cable 127.

Drive assembly 220 includes a distal drive rotor 222 and a motor 224 that drives rotation of distal drive rotor 222. Distal drive rotor 222 is configured to mate with inner drive core 140 of end effector assembly 100 upon engagement of end effector assembly 100 with handpiece assembly 200 to thereby engage distal drive rotor 222 and inner drive core 140 with one another. Cable 230 provides power and/or control signals to motor 224 to control rotation of distal drive rotor 222.

Outflow tubing 240 is configured such that, with end effector assembly 100 engaged with handle housing 210, outflow tubing 240 communicates with the internal lumen of inner cutting shaft 130 of end effector assembly 100 to receive resected tissue as well as fluid and other debris withdrawn from an internal surgical site during use. Outflow tubing 240 is configured to ultimately connect to a collection canister (not shown) or other suitable collection reservoir for collecting the tissue, fluid, and debris withdrawn from the internal surgical site. Outflow tubing 240 may additionally or alternatively couple to a suction source (not shown) for establishing suction through outflow tubing 240 and the with the internal lumen of inner cutting shaft 130 to facilitate drawing tissue, fluid, and debris into and through inner cutting shaft 130.

Inner drive core 140 extends proximally from proximal hub housing 110 of end effector assembly 100 and is configured to engage distal drive rotor 222 of a drive assembly 220. At least a portion of distal drive rotor 222 defines a non-circular cross-section that is complementary to that of the lumen of inner drive core 140 such that engagement of distal drive rotor 222 with inner drive core 140 rotationally fixes distal drive rotor 222 with inner drive core 140. In addition, inner drive core 140 extends distally through proximal hub housing 110 and is (directly or indirectly) fixedly engaged with proximal end portion 132 of inner cutting shaft 130 within proximal hub housing 110. Under such a configuration, rotation of inner drive core 140 imparts rotation to inner cutting shaft 130. Thus, with end effector assembly 100 engaged with handpiece assembly 200, motor 224 may be activated to drive rotation of distal drive rotor 222, thereby driving rotation of inner cutting shaft 130 relative to elongated outer shaft 120.

In order to engage end effector assembly 100 with handpiece assembly 200, end effector assembly 100, led by inner drive core 140, is inserted into handle housing 210 of handpiece assembly 200. Upon further insertion of end effector assembly 100 into handpiece assembly 200, inner drive core 140 is slid about distal drive rotor 222 to thereby rotatably engage distal drive rotor 222 and inner drive core 140 with one another.

Once tissue resecting device 10 is assembled, e.g., once end effector assembly 100 is engaged with handpiece assembly 200 as detailed above, tissue resecting device 10 is ready for use. In use, tissue resecting device 10 is positioned within an internal body cavity or organ, e.g., a uterus, such that the distal end portion of end effector assembly 100 is positioned adjacent tissue to be removed. Articulation cable 127 may be displaced to articulate the distal end portion of end effector assembly 100 to better position the distal end portion of end effector assembly 100 adjacent tissue to be removed. Tissue resecting device 10 may be inserted through an endoscope, e.g., a hysteroscope, or other device, or may be used independently.

Once tissue resecting device 10 is positioned adjacent tissue to be removed, tissue resecting device 10 is activated. Activation of tissue resecting device 10 drives motor 224 which rotationally drives drive rotor 222. Rotation of drive rotor 222, in turn, drives rotation of inner cutting shaft 130 relative to elongated outer shaft 120. Activation of tissue resecting device 10 also serves to activate suction through outflow tubing 240 (in embodiments where provided), thereby applying suction through inner cutting shaft 130. With such suction applied, tissue is drawn through window 128 of elongated outer shaft 120 and window 512 of cutting member 150 attached to inner cutting shaft 130, while cutting edge 500a and/or cutting edge 139 of tool portion 125 facilitates cutting of tissue as a result of the rotation of windows 512 relative to window 128. The suction also draws fluid and debris through inner cutting shaft 130. The tissue, fluid, and debris suctioned through inner cutting shaft 130 travel proximally through inner cutting shaft 130, inflow tubing 240, and ultimately, are deposited in a collection canister (not shown). Before, during, and/or after activation, articulation cable 127 may be displaced to articulate cutting member 150 to reposition cutting member 150 to remove additional tissue in different orientation(s). In particular, articulation of cutting member 150 may be effected while the plurality of blades 500 is being rotated.

Tissue resecting device 10 may be utilized until the desired tissue is removed from the internal body cavity or organ. Once the desired tissue is removed, tissue resecting device 10 may be deactivated and removed from the surgical site. Thereafter, end effector assembly 100 may be disengaged from handpiece assembly 200 and discarded (or sent for reprocessing), while handpiece assembly 200 is cleaned and/or sterilized for reuse.

As an alternative to handpiece assembly 200 configured for manual grasping and manipulation during use, tissue resecting devices 10 may alternatively be configured for use with a robotic surgical system wherein the end effector assembly 100 is configured to engage a robotic arm of the robotic surgical system in a similar manner as detailed above with respect to engagement of end effector assembly 100 with handpiece assembly 200. The robotic surgical system may employ various robotic elements to assist the surgeon and allow remote operation (or partial remote operation). More specifically, various robotic arms, gears, cams, pulleys, electric and mechanical motors, etc. may be employed for this purpose and may be designed with the robotic surgical system to assist the surgeon during the course of an operation or treatment. The robotic surgical system may include remotely steerable systems, automatically flexible surgical systems, remotely flexible surgical systems, remotely articulating surgical systems, wireless surgical systems, modular or selectively configurable remotely operated surgical systems, etc.

The robotic surgical system may be employed with one or more consoles that are next to the operating theater or located in a remote location. In this instance, one team of surgeons or nurses may prep the patient for surgery and configure the robotic surgical system with the surgical device disclosed herein while another surgeon (or group of surgeons) remotely control the surgical device via the robotic surgical system. As can be appreciated, a highly skilled surgeon may perform multiple operations in multiple locations without leaving his/her remote console which can be both economically advantageous and a benefit to the patient or a series of patients.

The robotic arms of the robotic surgical system are typically coupled to a pair of master handles by a controller. The handles can be moved by the surgeon to produce a corresponding movement of the working ends of any type of surgical instrument (e.g., end effectors, graspers, knifes, scissors, cameras, fluid delivery devices, etc.) which may complement the use of the tissue resecting devices described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. An end effector assembly of a tissue resecting device, comprising:
    a cutting member including:
        a core defining a passage; and
        a plurality of blades extending radially outward from the core, adjacent blades defining a gap therebetween, the plurality of blades defining at least one window in communication with the passage of the core; and
    an elongated outer shaft including a tool portion rotatably receiving the plurality of blades of the cutting member therein, the tool portion defining a lateral opening such that the plurality of blades of the cutting member rotatably received in the tool portion is in registration with the lateral opening, wherein the cutting member is transitionable between a neutral position, in which, the cutting member defines a longitudinal axis, and an articulated position, in which, at least a portion of the cutting member is offset from the longitudinal axis,
    wherein the tool portion of the elongated outer shaft includes a plurality of articulation members, adjacent articulation members defining a slit therebetween and wherein the slits defined in the tool portion are in registration with the respective gaps defined in the cutting member.

2. The end effector assembly according to claim 1, wherein the plurality of blades of the cutting member is arranged along a length of the core.

3. The end effector assembly according to claim 1, wherein the cutting member is rotatable between an open position, in which, the at least one window of the cutting member is in registration with the lateral opening of the elongated outer shaft, and a closed position, in which, the at least one window is offset relative to the lateral opening of the elongated outer shaft.

4. The end effector assembly according to claim 3, wherein the cutting member is rotatable in the articulated position.

5. The end effector assembly according to claim 1, wherein the cutting member is articulatable in a range of about 0 degree and about 90 degrees.

6. The end effector assembly according to claim 1, wherein each blade of the plurality of blades defining the at least one window includes a cutting edge configured to cut tissue.

7. The end effector assembly according to claim 1, wherein first and second windows of the at least one window of the plurality of blades diametrically oppose each other.

8. The end effector assembly according to claim 1, wherein first and second windows of the at least one window of the plurality of blades are arranged along at least a portion of a length of the cutting member.

9. The end effector assembly according to claim 1, wherein the cutting member includes a blunt tip distal of the plurality of blades.

10. The end effector assembly according to claim 1, wherein each slit extends away from the lateral opening.

11. The end effector assembly according to claim 1, wherein the elongated outer shaft further includes an articulation cable coupled to a distal portion of the elongated outer shaft, such that axial displacement of the cable causes articulation of the cutting member between the neutral position and the articulated position.

12. The end effector assembly according to claim 11, wherein the elongated outer shaft further includes a guide member configured to receive the articulation cable therethrough.

13. The end effector assembly according to claim 12, wherein the guide member is disposed on one articulation member of the plurality of articulation members.

14. An end effector assembly of a tissue resecting device, comprising:
   a cutting member including:
      a core defining a passage; and
      a plurality of blades extending radially outward from the core, adjacent blades defining a gap therebetween, the plurality of blades defining at least one window in communication with the passage of the core; and
   an elongated outer shaft including a tool portion rotatably receiving the plurality of blades of the cutting member therein, the tool portion defining a lateral opening such that the plurality of blades of the cutting member rotatably received in the tool portion is in registration with the lateral opening, wherein the cutting member is transitionable between a neutral position, in which, the cutting member defines a longitudinal axis, and an articulated position, in which, at least a portion of the cutting member is offset from the longitudinal axis, wherein the elongated outer shaft further includes a cable disposed along an outer peripheral surface thereof, the cable including a distal portion coupled to an outer peripheral surface of a distal portion of the elongated outer shaft, such that axial displacement of the cable along the outer peripheral surface of the elongated outer shaft transitions the cutting member between the neutral and articulated positions.

15. The end effector assembly according to claim 14, wherein the elongated outer shaft further includes at least one guide member disposed on the outer peripheral surface thereof configured to receive the articulation cable therethrough.

* * * * *